(12) United States Patent
Ankem

(10) Patent No.: US 8,454,707 B2
(45) Date of Patent: Jun. 4, 2013

(54) BIOMEDICAL IMPLANTABLE MATERIAL AND METHODS OF PRODUCING THE SAME

(75) Inventor: Sreeramamurthy Ankem, Silver Spring, MD (US)

(73) Assignee: University of Maryland, College Park, MD (US)

( * ) Notice: Subject to any disclaimer, the term of this patent is extended or adjusted under 35 U.S.C. 154(b) by 231 days.

(21) Appl. No.: 12/754,309

(22) Filed: Apr. 5, 2010

(65) Prior Publication Data

US 2011/0009965 A1    Jan. 13, 2011

Related U.S. Application Data

(60) Provisional application No. 61/166,463, filed on Apr. 3, 2009, provisional application No. 61/240,024, filed on Sep. 4, 2009.

(51) Int. Cl.
*A61F 2/28* (2006.01)
(52) U.S. Cl.
USPC ........................................ 623/23.55; 623/1.39
(58) Field of Classification Search
USPC .................. 623/23.53–23.55, 1.15, 1.39, 1.4
See application file for complete search history.

(56) References Cited

U.S. PATENT DOCUMENTS

| | | | |
|---|---|---|---|
| 3,334,210 A | 8/1967 | Williams et al. | |
| 3,852,045 A * | 12/1974 | Wheeler et al. | 428/566 |
| 4,179,485 A | 12/1979 | Tritten | |
| 4,547,327 A | 10/1985 | Bruins et al. | |
| 4,865,603 A | 9/1989 | Noiles | |
| 4,870,243 A | 9/1989 | Wilson et al. | |
| 5,177,037 A | 1/1993 | Schuldies | |
| 5,348,788 A | 9/1994 | White | |
| 5,545,220 A * | 8/1996 | Andrews et al. | 623/8 |
| 5,697,997 A | 12/1997 | Aronsson et al. | |
| 5,725,580 A | 3/1998 | Cloutier et al. | |
| 5,843,289 A | 12/1998 | Lee et al. | |
| 6,183,255 B1 | 2/2001 | Oshida | |
| 6,225,589 B1 | 5/2001 | Bartok | |
| 6,387,121 B1 | 5/2002 | Alt | |
| 6,447,550 B1 | 9/2002 | Hunter et al. | |

(Continued)

FOREIGN PATENT DOCUMENTS

EP    0 606 566    7/1994

OTHER PUBLICATIONS

Peng et al. "Effect of Electrical-Discharging on Formation of Nanoporous Biocompatible Layer on Titanium," *Journal of Alloys and Compounds*, vol. 492, Issues 1-2, pp. 625-630, Mar. 4, 2010.

(Continued)

*Primary Examiner* — Thomas J Sweet
*Assistant Examiner* — Jason-Dennis Stewart
(74) *Attorney, Agent, or Firm* — Arent Fox LLP

(57) ABSTRACT

The present invention relates to improved biomedical implantable material comprising a plurality of pores, of which one or more of the pores are interconnected below the surface of the material. The improved biomedical implantable material may be used in biomedical implant devices such as orthopedic implants, spinal implants, neurocranial implants, maxillofacial implants, and joint replacement implants. The present invention also relates to a method of preparing an improved biomedical implantable material, comprising subjecting an implantable material to a pore-forming treatment and optionally further subjecting the material to a surface-modifying treatment. The biomedical implantable material may be used in other applications, which as applications where two surfaces are contacted and bonding between the surfaces is required.

17 Claims, 7 Drawing Sheets

U.S. PATENT DOCUMENTS

| | | |
|---|---|---|
| 7,018,418 B2 | 3/2006 | Amrich et al. |
| 7,208,222 B2 | 4/2007 | Rolfe et al. |
| 7,335,314 B2 | 2/2008 | Wu |
| 7,635,447 B2 | 12/2009 | Hamman et al. |
| 2007/0154514 A1* | 7/2007 | Demakas et al. ............. 424/423 |
| 2007/0225785 A1* | 9/2007 | Park et al. .................... 607/116 |

OTHER PUBLICATIONS

Chen et al. "Effect of Electro-Discharging on Formation of Biocompatible Layer on Implant Surface." *Journal of Alloys and Compounds*, vol. 456, Issues 1-2, pp. 413-418, May 29, 2008.

* cited by examiner

US 8,454,707 B2

BIOMEDICAL IMPLANTABLE MATERIAL AND METHODS OF PRODUCING THE SAME

This application is Non-Provisional application which claims priority to provisional application No. 61/240,024, filed Sep. 4, 2009, and provisional application No. 61/166,463, filed Apr. 3, 2009, the entire specification claims and drawings of which are incorporated herewith by reference.

This invention was made with government support under contract number CMMI0733522 awarded by NSF. The government has certain rights in this invention.

FIELD OF THE INVENTION

The present invention provides a biomedical implantable material for use in implants, such as orthopedic implants, and methods of making the same.

BACKGROUND OF THE INVENTION

Biomedical implants, such as hip replacement joints and orthopedic implants, have been beneficial to patients with degenerative disease and patients suffering from disabling injuries. Implant surgeries are often very costly and painful, and result in a long recovery period. Many patients with implants are often required to undergo at least one additional surgery, called a revision surgery, after a period of time. Revision surgeries are often necessary when the existing implant, after time, fails to perform its function properly and/or causes pain to the patient. For example, some orthopedic implants, such as hip implants, loosen from the bone after 10 to 15 years and require replacement. Patients with failed implants such as these are often elderly and in a weakened physical state, which can augment the risks associated with major surgery.

One of the main causes of low implant longevity is a poor implant-to-bone bonding, or interfacial strength. Implants made of materials which do not sufficiently accommodate bone cell growth can form a weak implant-bone interface. Research and development efforts have resulted in some improvement in this area. For example, there have been improvements in implant coatings and non-controlled porous surface modification.

Sintering is a method that can be utilized to create pores on the surface of an implantable material. U.S. Pat. No. 7,635,447 discloses a method of providing a porous metal implant by sintering mixtures. U.S. Pat. No. 4,547,327 discloses a method of providing a porous oral prosthesis by means of sintering polymeric particles. U.S. Pat. No. 4,179,485 discloses a method of providing a porous aluminum implant wherein grains of alumina are subjected to firing, compression, and sintering.

Laser etching and plasma gas surface etching have also been used to create pores. U.S. Pat. No. 7,018,418 discloses a method of creating micro-recesses on the surface of an implant by means of laser etching. U.S. Pat. No. 5,843,289 discloses a method of creating surface porosity by means of plasma gas etching.

However, such methods, which involve the creation of pores in an uncontrolled fashion, have failed to adequately meet the need in the art to provide biomedical implants made of implantable material which demonstrate improved longevity and durability and can improve the quality of life and reduce medical costs.

The biomedical implantable material of the present invention meets the unmet need in the art by providing a material which enhances bonding between a bone and an implant.

SUMMARY OF THE INVENTION

The present invention provides a biomedical implantable material comprising a plurality of pores, wherein two or more of the pores are interconnected below the surface of the material. The present invention also provides biomedical implant devices comprising the biomedical implantable material.

The present invention further provides processes for producing an improved biomedical implantable material, comprising subjecting an implantable material to a pore-forming treatment, and optionally further subjecting the implantable material to a surface-modifying treatment.

BRIEF DESCRIPTION OF THE DRAWINGS

FIG. 2A shows an area of the titanium disk, including six pores. FIG. 2B shows a view looking down a pore.

FIG. 3A shows the internal pore surface morphology before thermal oxidation. FIG. 3B shows the internal pore surface morphology after thermal oxidation.

FIG. 4A shows the implantable material before thermal oxidation. FIG. B shows the implantable material after thermal oxidation.

DETAILED DESCRIPTION OF THE INVENTION

Figure 1:
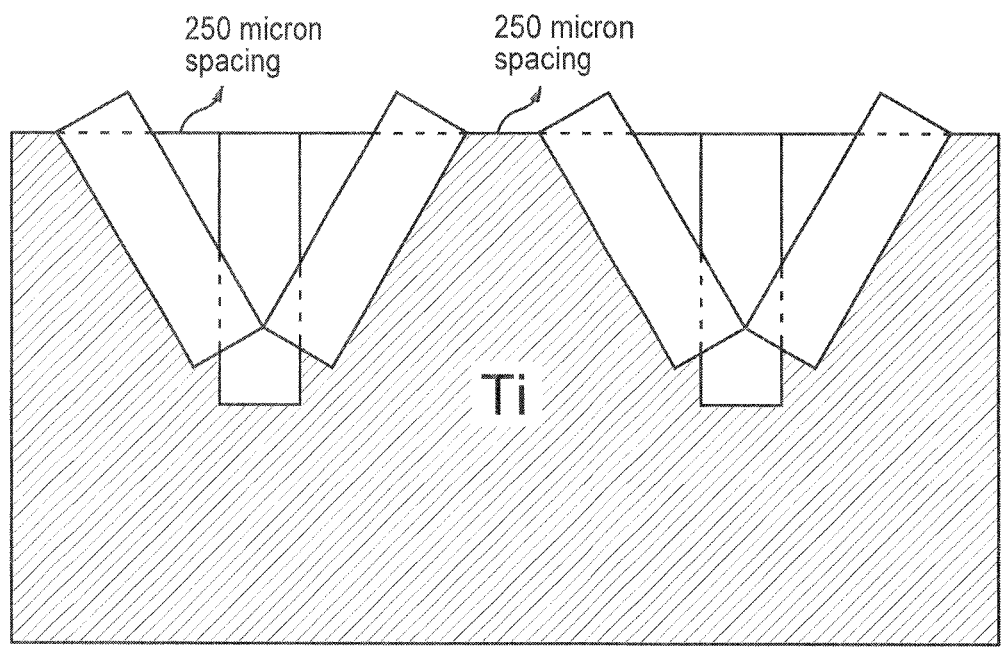
FIG. 1 shows a schematic diagram of the implantable material described in Example 1.

The present invention provides a biomedical implantable material comprising a plurality of pores, wherein two or more of the pores are interconnected below the surface of the material. The present invention also provides biomedical implant devices comprising the biomedical implantable material.

The biomedical implantable material can comprise any material that is biocompatible and can be implanted into a patient's body. The biomedical implantable material preferably comprises a metal or metal alloy. In preferred embodiments, the implantable material comprises at least one component selected from the group consisting of: titanium, cobalt, chromium, tantalum, stainless steel, nickel, zirconium, and aluminum. The biomedical implantable material may also comprise alloys of one or more of these components. In preferred embodiments, the implantable material comprises titanium or an alloy of titanium.

The biomedical implantable material of the present invention comprises a plurality of pores, or holes, of which two or more pores are interconnected below the surface of the material. In preferred embodiments, the pores are "micropores," or pores having a micron-level diameter. In preferred embodiments, the pores have a diameter of about less than 1,000 microns, preferably about 100 to about 500 microns, and more preferably about 200 to about 400 microns. In some preferred embodiments, the pores have a diameter of about 250 microns. In preferred embodiments, the pores have a depth of less than 5,000 microns, preferably about 250 microns to about 3,000 microns, more preferably about 500 microns and 1,500 microns, and most preferably about 600 to 900 microns.

In some embodiments, the pores in the implantable material are of uniform size and angle relative to the surface and/or uniformly spaced (or equidistant to each other) throughout the surface of the material. In other embodiments, the pores vary in size and angle relative to the surface and/or are present throughout the surface of material in a non-uniform manner. The pores may be perpendicular to the surface of the material, or they may be angled relative to the surface. Pores which are perpendicular are generally at about a 90° angle relative to the surface of the materials. Pores which are angled are generally at between 0° to 90°, or between 90° to 180°, relative to the surface of the materials. In preferred embodiments where the pores are angled, the pores are at angled between 0° to 90° relative the surface, preferably about 10° to about 80°, more preferably about 25° to about 75°, and most preferably about 30° to about 50°. The pores may be all perpendicular, all angled, or a combination of perpendicular and angled.

The pores are preferably spaced apart from each other at a distance of about less than 1000 microns, preferably about 100 to about 500 microns, and more preferably about 200 to about 400 microns. The pores may be uniformly spaced and equidistant from each other, but they may be spaced in a non-uniform manner. In preferred embodiments, the pores are uniformly spaced, preferably at a distance of about 250 microns from each other.

In some preferred embodiments, the pores have similar dimensions (diameter and depth), are uniformly spaced throughout the surface of the material, and demonstrate a pattern of angled and perpendicular pores. For example, in some embodiments, there is one perpendicular pore between every four angled pores.

A pore is "interconnected" to another pore when the pore is joined to the second pore at one or more portions of the pore. In some embodiments, one pore is connected to another pore via a channel under the surface of the materials which connects the two pores. In some embodiments, the bases of one or more pores are connected to any portion of another pore. In preferred embodiments, the pores are not interconnected at the surface of the materials. The interconnection of the pores preferably occurs under the surface of the materials, about less than 5,000 microns, preferably about 250 microns to about 3,000 microns, more preferably about 500 microns and 1,500 microns, and most preferably about 600 to 900 microns, under the surface of the materials. The pores may be interconnected at any portion. For example, a pore may be interconnected to any part of a second pore, such as in the middle of the length of the pore, or at the base of the pore. In some preferred embodiments, the pores are present on all surfaces that contact another surface, such as a bone. In some embodiments, the surfaces comprising the interconnected pores are flat or curved, depending on the application.

In preferred embodiments, of the total number of pores in the implantable material, more than about 10%, preferably more than about 25%, more preferably more than about 50% and most preferably, more than about 75% of the pores are interconnected with one or more other pores. In some preferred embodiments, about 90% to about 100% of the pores are connected to one or more other pores. Most preferably, essentially all of the pores are connected to one or more other pores.

In some embodiments, the implantable material contains two or more groups of interconnected pores. Each group of interconnected pores present in the implantable material may contain the same number or a different number of pores. In some preferred embodiments, the implantable material contains groups each containing 2 to 20 interconnected pores, preferably 3 to 10 interconnected pores, and most preferably 5 interconnected pores. In embodiments where the implantable material contains groups of 5 interconnected pores, preferably four pores are angled pores, and the fifth pore is a perpendicular pore. In some embodiments, the implantable material contains groups of 3 interconnected pores, and preferably two pores are angled pores, and the third pore is a perpendicular pore. An example of such an arrangement is shown in FIG. 1.

The biomedical implantable material of the present invention demonstrates improved properties over other implantable materials in the art. The improved properties may include, but are not limited to, improved interlocking between the implant and the bone, improved load transfer between the base implant and modified surface layer and bone, improved bone stimulation, and increased longevity of implant containing the implantable material. Unlike other implantable materials in the art, which do not contain interconnected pores under the surface, the implantable materials of the present invention demonstrate improved implant-bone interfacial strength, as the bone cells are able to form bonds below the surface of the material and "interlock." In preferred embodiments, the biomedical implantable material is utilized in an implant which is contacted with a surface which accommodates bone cell growth. The strength of the implant-bone bond is enhanced when the pores have an increased "nano-roughness" (roughness of surface on a nanoscale level) or surface modification to create increased surface area. The bone of the patient is able to grow into the interconnected pores and interlock with the implant, and the surface modification allows for increased surface area for the bone to contact. In some embodiments, a bone cement material is applied to the implantable material, and the implantable material is contacted with the bone. In preferred embodiments, the pores have an average nano-roughness of up to 1000 nm, more preferably about 150 nm to about 750 nm, and most preferably about 200 nm to about 500 nm.

In many cases, unlike patients receiving other, known implants, a patient receiving an implant comprising the biomedical implantable material of the present invention may not require painful and expensive revision surgeries to repair or replace failed implant devices, as the implants of the present invention have increase durability and longevity.

In preferred embodiments, the biomedical implantable material is a solid material which forms the implant. For example, in some preferred embodiments, the implantable material may be a solid material, such as titanium or an alloy of titanium, which is treated to form interconnected pores, and then implanted into a patient. This preferred embodiment demonstrates advantages over embodiments wherein the biomedical implantable material forms a sheet which is treated and then subsequently placed over an implant. Such embodiments, while still useful, require additional steps and result in additional complications, as the sheet would need to be bonded to the implant. In addition, there may be some decreased durability with these embodiments.

The biomedical implantable devices of the present invention may include orthopedic implants for the hips, knees, acetabular cups, ankles, or shoulders; spinal implants; neurocranial implants; maxillofacial implants; dental implants; and joint replacement implants. Preferably the implantable device is implanted near or in the bone of a patient and contacts the bone. In preferred embodiments, the implantable device is an orthopedic implant or joint replacement implant.

The biomedical implantable material may be used in other applications. For example, the material, which has interconnected pores, may be used in any application where two surfaces are contacted and bonding between the surfaces is required.

The present invention further provides processes for producing an improved biomedical implantable material, comprising subjecting an implantable material to a pore-forming treatment, and optionally further subjecting the implantable material to a surface-modifying treatment.

The "pore-forming treatment" of the present invention is any treatment which results in the creation of interconnected pores in the implantable material. The pores are interconnected preferably below the surface of the materials. In preferred embodiments, the pore-forming treatment comprises at least one of the following procedures: electrical discharge machining, plasma processing, mechanical drilling, sintering, laser etching, plasma gas etching, or gritt blasting. The pore-forming treatment may be applied by any methods known in the art, such as those described in U.S. Pat. Nos. 7,635,447; 4,547,327; 4,179,485; 7,018,418; 5,843,289; 7,335,314; 4,865,603; 5,348,788; and 7,208,222, all of which are incorporated by reference in their entireties. Peng et al. "Effect of Electrical-Discharging on Formation of Nanoporous Biocompatible Layer on Titanium," *Journal of Alloys and Compounds*, Vol. 492, Issues 1-2, pp. 625-630, 4 Mar. 2010, and Chen et al. "Effect of Electro-Discharging on Formation of Biocompatible Layer on Implant Surface." *Journal of Alloys and Compounds*, Vol. 456, Issues 1-2, pp. 413-418, 29 May 2008, incorporated by reference in their entireties, also describe methods of pore-forming. In preferred embodiments, the pore-forming treatment also modifies the surface of the materials, creating "surface roughness" or "nano-roughness." In some embodiments, the "nano-roughness" of the implantable material after the pore-forming treatment is up to 1,000 nm, more preferably about 150 nm to about 750 nm, and most preferably about 200 nm to about 500 nm.

In preferred embodiments, the pore-forming treatment is a controlled process, with the purpose of creating a plurality of pores in which two or more of the pores are interconnected under the surface of the material.

In preferred embodiments, the pore-forming treatment comprises electrical discharge machining (EDM), which is also known as spark machining, spark eroding, die sinking or wire erosion. The EDM process may be accomplished by any known method of EDM in the art, such as those described in U.S. Pat. Nos. 3,334,210; 4,870,243; 5,177,037; 5,725,580; and 6,225,589, which are each incorporated by reference in their entireties. The EDM process is preferably computer-automated, as the pore-forming treatment is conducted in a controlled, deliberate fashion, wherein the formation of the interconnected pores under the surface of the materials is the goal. One of ordinary skill in the art will understand how to create interconnected pores by the EDM.

The process for producing an improved biomedical implantable material may further comprise an optional step of subjecting the implantable material to a surface-modifying treatment. The "surface-modifying treatment" of the present invention is any treatment which modifies the surface qualities of the implantable material. In preferred embodiments, the surface-modifying treatment modifies the surface qualities of the implantable materials by creating or enhancing the nano-roughness of the surface, thereby increasing the surface area. The surface-modifying treatment may create or enhance nano-roughness on any surface is contacts, including the surface of the implantable material and the surface of the individual interconnected pores. In preferred embodiments, the surface-modifying treatment comprises thermal oxidation, or can be accomplished by various polymerization methods and/or electrolytical methods. As discussed above, the pore-forming treatment can cause some surface modification. The optional step of surface modification can enhance the beneficial properties of the implantable material which comprises interconnected pores and further increase nano-roughness. Implantable materials which are subjected to both the pore-forming treatment and the surface-modifying treatment typically demonstrate improved bonding capabilities, and increased longevity and durability.

In preferred embodiments, after the surface-modifying treatment, the nano-roughness of the implantable material is increased by up to 500%, more preferably about 50% to about 250%, and most preferably about 100% to about 200%.

In embodiments wherein the surface-modifying treatment is thermal oxidation, the thermal oxidation may be performed by any known method in the art, for example, U.S. Pat. Nos. 5,697,997; 6,183,255; and 6,447,550, and European Patent No. 0 606 566, each of which are incorporated by reference in their entirety. In preferred embodiments, the implantable material is subjected to forced air. "Forced air" refers to air which is applied at preferably up to 3 atm. The "air" may be ambient air, commercially pure oxygen, or any oxygen-enriched air. The thermal oxidation occurs at a temperature of preferably up to 1000° C., more preferably about 100° C. to about 900° C., and most preferably about 200° C. to about 500° C. In some preferred embodiments, the thermal oxidation occurs at a temperature of about 250° C. The thermal oxidation preferably occurs until an oxide layer is formed but most or all of the pores remain unoccluded. In preferred embodiments, the thermal oxidation occurs for a period of about 30 seconds to about 10 hours, more preferably about 1 minute to about 60 minutes, and most preferably about 5 minutes to about 30 minutes. In some embodiments, wherein the thermal oxidation occurs at a temperature of about 200° C. to about 500° C., the thermal oxidation occurs for a period of about 5 to about 60 minutes. In some embodiments, wherein the thermal oxidation occurs at a temperature of about 250° C., the thermal oxidation may occur for a period of about 30 minutes. In some other embodiments, wherein the thermal oxidation occurs at a temperature of about 200° C., the thermal oxidation may occur for a period of about 60 minutes. In some other embodiments, wherein the thermal oxidation occurs at a temperature of about 500° C., the thermal oxidation may occur for a period of about 5 minutes.

In some embodiments, where the biocompatible material comprises titanium or an alloy of titanium, the thermal oxidation may form a layer of titanium oxide, which is a biocompatible material.

All references cited herein are incorporated by reference in their entirety.

EXAMPLE 1

A 2 mm thick×12.7 mm diameter CP Grade 4 disk comprising titanium was subjected to electro-discharging machining to create six perpendicular and angled pores. FIG. 1 shows a schematic diagram showing the expected pore or hole configuration geometry, as made by the electro-discharging machining (EDM) technique. FIG. 1 shows that the pore diameter is 250 microns, and the pores are spaced 250 microns apart. Two angled pores, which are at a 30° angle with respect to the surface, are interconnected to a perpendicular pore. The pores have a depth of about 1 mm. The nano-roughness of the surface of the pores after electro-discharging machining treatment is about 225 nm. After treatment with thermal oxidation at 250° C. under forced air, a layer of titanium oxide is formed on the surface of the pores, which have a nano-roughness of about 400 nm.

Figure 2A:
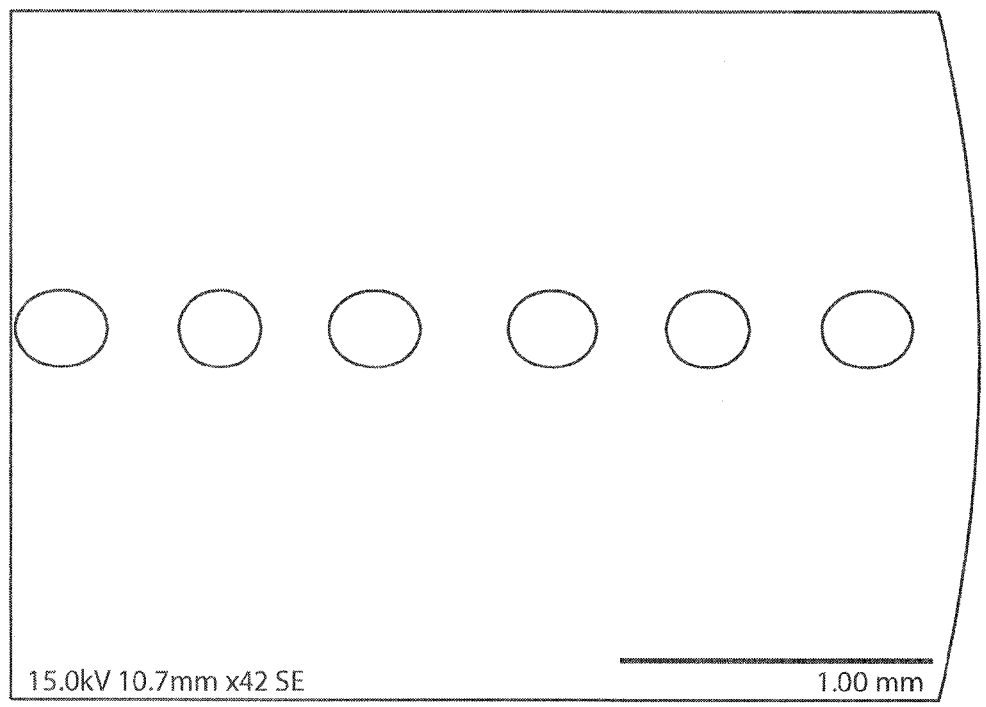
FIGS. 2A and 2B show a scanning electron micrograph of the implantable material described in Example 1.
Figure 2B:
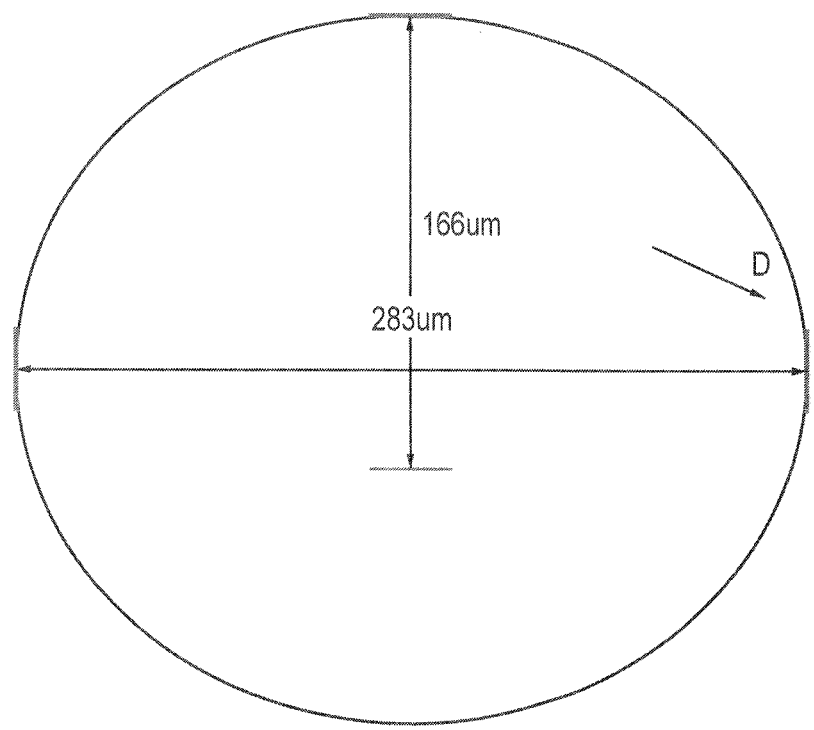
Figure 3A:
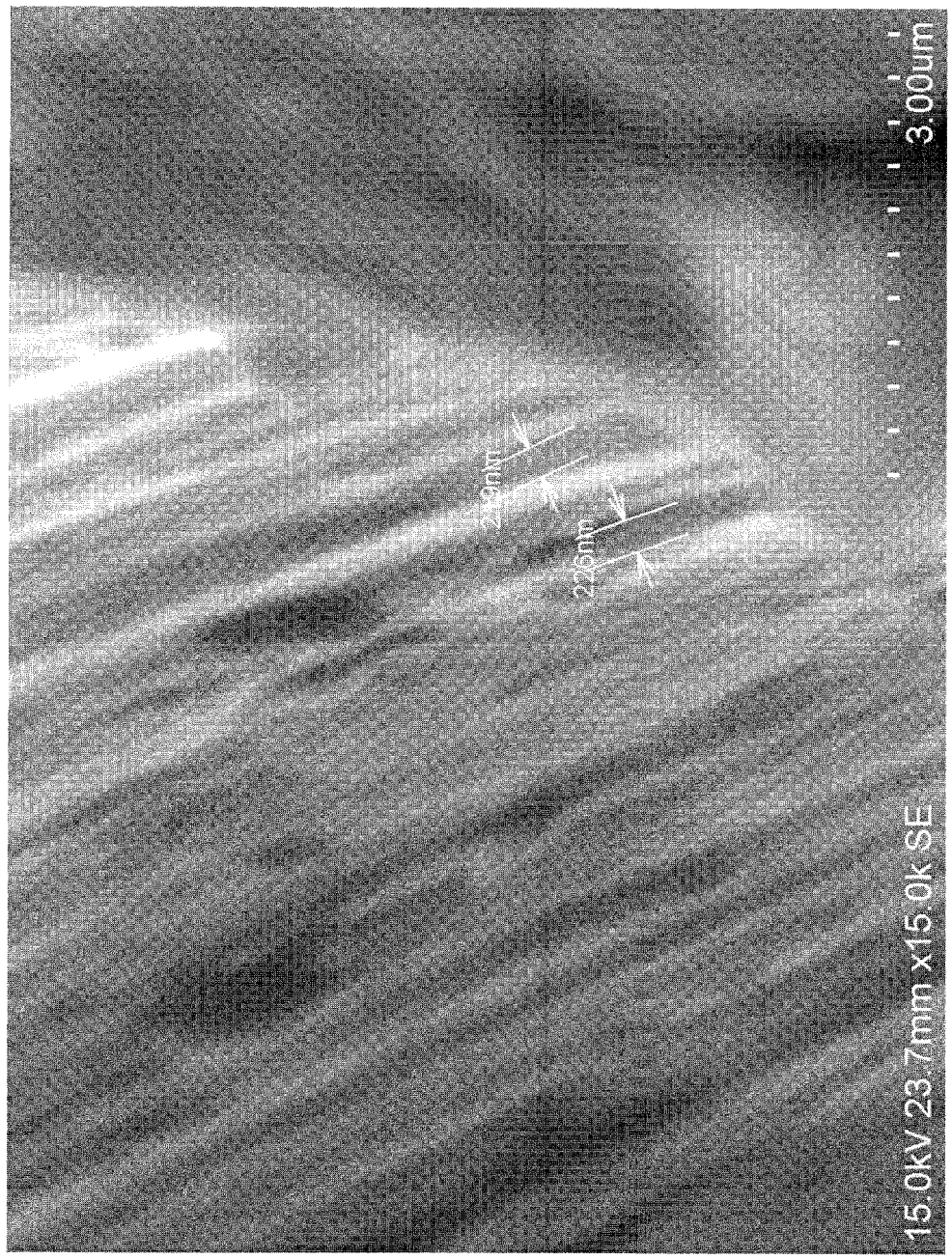
FIGS. 3A and 3B show a scanning electron micrograph of the implantable material described in Example 1.
Figure 3B:
Figure 4A:
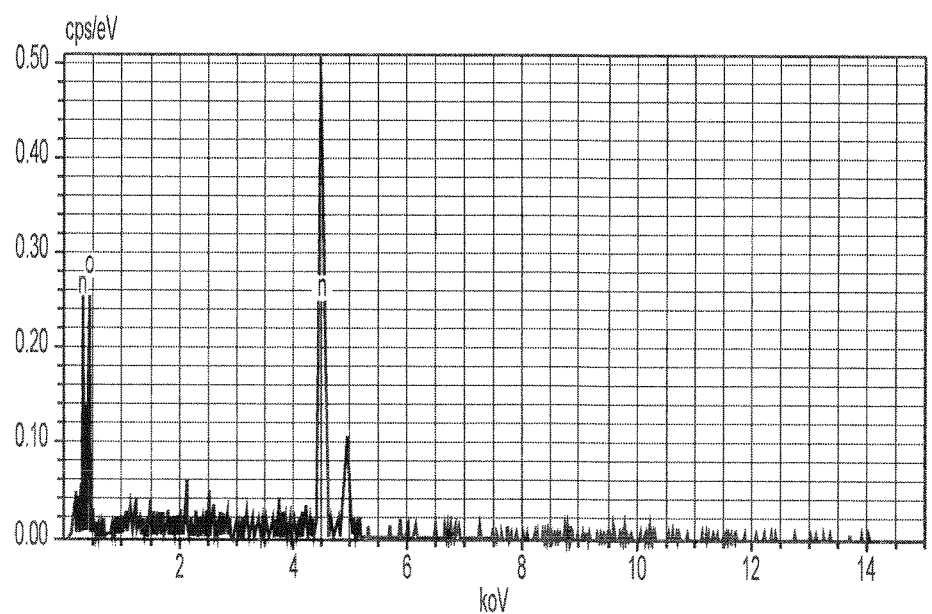
FIG. 4A and FIG. 4B show X-ray diffraction peaks of the implantable material described in Example 1.
Figure 4B:
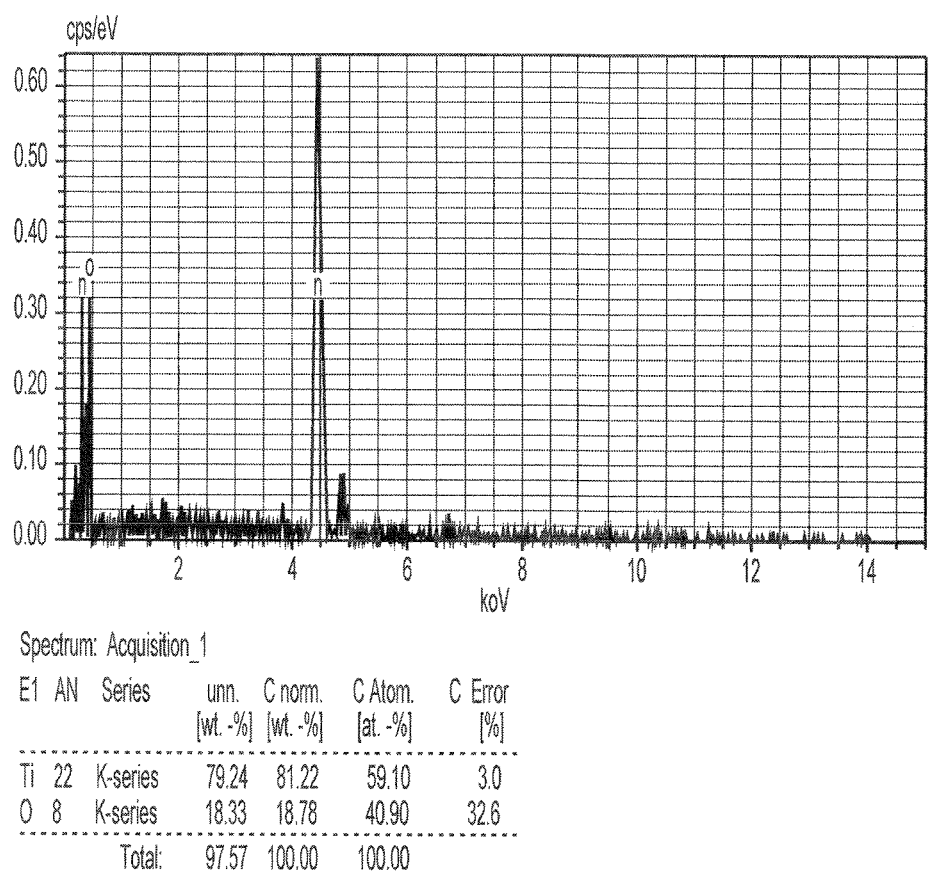

The pore morphology, including nano-roughness, was characterized by scanning electron microscopy (SEM) and x-ray diffraction (XRD). FIGS. 2A, 2B, 3A, and 3B show a SEM micrograph of the implantable material. FIG. 2A shows the pores created by the EDM treatment; the geometry of the pores approximately corresponds to the geometry of the pores shown in FIG. 1. FIG. 2B shows the view looking down one of the pores shown in FIG. 2A. The intersection of the angled pore with the perpendicular pore is indicated by the arrow. FIG. 3A shows the internal pore surface morphology corresponding to the location "D" as shown in FIG. 2B, before thermal oxidation. The nano-roughness of the material resulting from the EDM treatment is about 225 nm. FIG. 3B shows the same area as FIG. 3A, after thermal oxidation. FIGS. 4A and 4B show XRD peaks. FIG. 4A shows the XRD peaks of the pore walls shown in FIG. 3A. The chemical analysis indicates the expected presence of a thin titanium oxide layer before thermal oxidation. FIG. 4B shows the XRD peaks of the pore wall shown in FIG. 3B, after thermal oxidation. FIG. 4B shows the significant increase in oxygen content near the surface of the thermally oxidized specimen, which is consistent with the increase in nano-roughness.

What is claimed:

1. A biomedical implantable material comprising a plurality of pores, wherein the pores are formed from the surface of the material into the material and two or more of the pores are directly connected below the surface of the material and wherein one or more of the pores are at an angle of about 90° relative to the surface of the material and the other pores are at an angle other than 90° relative to the surface of the material.

2. The biomedical implantable material of claim 1, wherein the pores have a diameter of 200 to 400 microns.

3. The biomedical implantable material of claim 1, wherein the pores have a depth of 600 to 900 microns.

4. The biomedical implantable material of claim 1, wherein 90% or more of the pores are interconnected to one or more other pores below the surface of the materials.

5. The biomedical implantable material of claim 1, wherein the pores are uniformly spaced from each other.

6. The biomedical implantable material of claim 1, wherein the material comprises one or more components selected from the group consisting of: titanium, cobalt, chromium, tantalum, stainless steel, nickel, zirconium, vanadium, aluminum, and alloys thereof.

7. The biomedical implantable material of claim 1, wherein the material comprises titanium or alloys of titanium.

8. A biomedical implant device comprising the biomedical implantable material of claim 1.

9. The biomedical implant device of claim 8, wherein the device is selected from the group consisting of: orthopedic implants for the hips, knees, acetabular cups, ankles, or shoulders; spinal implants; neurocranial implants; maxillofacial implants; dental implants; and joint replacement implants.

10. A process for preparing an improved biomedical implantable material, comprising subjecting an implantable material to a pore-forming treatment to form a plurality of pores, wherein the pores are formed from the surface of the material into the material in such a manner that two or more of the pores are directly connected below the surface of the implantable material and one or more of the pores are at an angle of about 90° relative to the surface of the material and the other pores are at an angle other than 90° relative to the surface of the material.

11. The process of claim 10, further comprising subjecting the implantable material to a surface-modifying treatment.

12. The process of claim 11, wherein the surface-modifying treatment comprises thermal oxidation.

13. The process of claim 12, wherein the thermal oxidation occurs at a temperature of about 100° C. to about 300° C.

14. The process of claim 12, wherein the thermal oxidation comprises subjecting the material with forced air, wherein the air is atmospheric air, commercially pure oxygen, or oxygen-enriched air.

15. The process of claim 12, wherein the thermal oxidation occurs over a time period of about 5 to about 60 minutes.

16. The process of claim 10, wherein the pore-forming treatment is selected from the group consisting of: electrical discharge machining, plasma processing, mechanical drilling, sintering, laser etching, plasma gas etching, and gritt blasting.

17. The process of claim 10, wherein the pore-forming treatment comprises electrical discharge machining.

* * * * *